US008694091B2

(12) United States Patent  
Birk et al.

(10) Patent No.: US 8,694,091 B2
(45) Date of Patent: Apr. 8, 2014

(54) IN VIVO DETERMINATION OF ACIDITY LEVELS

(75) Inventors: Uzi Birk, Huddinge (SE); David Livshits, San Francisco, CA (US)

(73) Assignee: DeLaval Holding AB, Tumba (SE)

( * ) Notice: Subject to any disclaimer, the term of this patent is extended or adjusted under 35 U.S.C. 154(b) by 0 days.

(21) Appl. No.: 13/822,007

(22) PCT Filed: Sep. 28, 2011

(86) PCT No.: PCT/SE2011/051154
§ 371 (c)(1),
(2), (4) Date: Mar. 11, 2013

(87) PCT Pub. No.: WO2010/047150
PCT Pub. Date: Apr. 12, 2012

(65) Prior Publication Data
US 2013/0178721 A1      Jul. 11, 2013

Related U.S. Application Data (60) Provisional application No. 61/389,351, filed on Oct. 4, 2010.

(30) Foreign Application Priority Data

Oct. 4, 2010   (SE) ....................... 1051030

(51) Int. Cl.
*A61B 5/00* (2006.01)
(52) U.S. Cl.
USPC .......................................... 600/547
(58) Field of Classification Search
USPC ................................. 600/547, 593
See application file for complete search history.

(56) References Cited

U.S. PATENT DOCUMENTS

| 5,583,432 | A | 12/1996 | Barnes |
| 6,059,733 | A | 5/2000 | Brune et al. |
| 7,938,775 | B2 * | 5/2011 | Rabinovitz et al. ........... 600/309 |
| 8,517,961 | B2 * | 8/2013 | Imran et al. ................... 600/593 |
| 2002/0128542 | A1 | 9/2002 | Van Over |
| 2002/0156356 | A1 | 10/2002 | Mehrotra |

(Continued)

FOREIGN PATENT DOCUMENTS

| AU | 428 035 B2 | 9/1972 |
| DE | 29 24 753 A1 | 1/1981 |

(Continued)

OTHER PUBLICATIONS

International-Type Search Report, dated Apr. 18, 2011, from corresponding PCT application.

(Continued)

*Primary Examiner* — Max Hindenburg
(74) *Attorney, Agent, or Firm* — Young & Thompson (57) ABSTRACT

A bolus for use in a ruminant animal's reticulum includes a cavity (100) configured to receive ruminal fluids present in the stomach. The cavity has walls (110) of a dielectric material and is encircled by a coil member (120), which is configured to subject the ruminal fluids to an electro-magnetic field. A Sensor element (310) measures the electromag-netic field's influence on the ruminal fluids and thus register an electromagnetic property representative of an acidity level of said fluids. A transmitter (410) transmits a wireless output signal (SD) reflecting the acidity measure.

21 Claims, 3 Drawing Sheets

(56) References Cited

U.S. PATENT DOCUMENTS

| | | |
|---|---|---|
| 2004/0133131 A1 | 7/2004 | Kuhn et al. |
| 2006/0231110 A1 | 10/2006 | Mintchev |
| 2007/0088194 A1 | 4/2007 | Tahar et al. |
| 2008/0236500 A1 | 10/2008 | Hodges et al. |
| 2009/0187392 A1 | 7/2009 | Riskey et al. |
| 2009/0281395 A1 | 11/2009 | Semler et al. |
| 2010/0016756 A1 | 1/2010 | Tahar |
| 2010/0045309 A1 | 2/2010 | Zou et al. |

FOREIGN PATENT DOCUMENTS

| | | |
|---|---|---|
| GB | 2 455 700 A | 6/2009 |
| RU | 8584 | 12/1998 |
| RU | 2223033 C2 | 2/2004 |
| SU | 326793 A | 12/1975 |
| SU | 486742 A | 1/1976 |
| WO | 01/13712 A1 | 3/2001 |
| WO | 2006/001020 A2 | 1/2006 |

OTHER PUBLICATIONS

International Search Report, dated Mar. 23, 2012, from corresponding PCT application.

Supplementary International Search Report, dated Jan. 17, 2013, from corresponding PCT application.

Thermpon Ativanichayaphong et al., An Implantable Batteryless Wireless Impedance Sensor for Gastroesophageal Reflux Diagnosis, IEEE, 2010, pp. 608-611.

* cited by examiner

IN VIVO DETERMINATION OF ACIDITY LEVELS

THE BACKGROUND OF THE INVENTION AND PRIOR ART

The present invention relates generally to automatic in vivo de-termination of acidity measures in body fluids. More particularly the invention relates to a bolus according to the preamble of claim 1 and a method according to the preamble of claim 9. The invention also relates to a computer program according to claim 12 and a computer readable medium according to claim 13.

To accomplish an efficient and animal friendly livestock handling it is important to monitor the animals' physiological state and health condition. Of course, to this aim, regular farmer's inspections and veterinary examinations can never be excluded. However, as a complement thereto and to provide an ongoing supervision, various automatic systems can be employed. One example of such a solution involves introducing a so-called bolus into the animal's stomach. More precisely, the bolus should preferably be placed in the reticulum, and normally the bolus has a weight of around 50-200 grams in order not to be forwarded through the digestive system. Once installed in the animal, the bolus may register various health-related parameters of the animal and report corresponding data to an external station via a radio interface.

U.S. Pat. No. 6,059,733 discloses a method of determining a physiological state of a ruminant animal using an ingestible bolus. The bolus includes a temperature sensor and a transmitter. Thus, core body temperatures within the animal's stomach can be registered and reported to a remote receiver for mathematical analysis. As a result, the physiological state of the animal can be determined.

US 2007/0088194 describes a bolus for introducing into a ruminant animal's reticulum. The bolus contains an acoustic sensor for receiving acoustic signals emanated by various signal sources in the animal, such as the heart and respiratory organs, and output values indicative of the animal's health condition.

US 2010/0045309 reveals a fluid sensor for use within the gastro-intestinal tract of a human being. The sensor includes a sensing coil which is immersible in the sample fluid of the gastro-intestinal tract; a signal generator in electrical with the sensing coil for applying an electrical current pulse to the sensing coil; a signal receiver in communication with the sensing coil for measuring an electrical reflection relative to said electrical current pulse; and a data processor for receiving the electrical reflection and for calculating data representative of at least one property, such as pH of the sample fluid based on the electrical reflection. The fluid sensor can also include a reference coil for calibrating the sensing coil. The sensor coil and reference coil can be encapsulated in a swallowable pill shell. Thus, as such, an acidity sensor is known, which operates based on electromagnetic field influencing.

Problems Associated with the Prior Art

Hence, although various monitoring solutions are known in the prior that involve ingested sensors and remote monitoring, there is yet no solution for ongoing measurement of the pH-level of an animal's stomach fluids, which both provides a reliable measure of the pH-level in the stomach and is highly convenient to use. Monitoring the pH-level in the stomach is important, since this measure is an early indicator of incorrect food intake as well as various stomach diseases. Measuring pH in an animal's stomach is challenging for many reasons, for instance due to the harsh environment that the equipment must withstand; because frequent and complicated sensor calibration is required; and at the same time, the measurements should not cause unnecessary inconveniences for the animal.

SUMMARY OF THE INVENTION

The object of the present invention is to alleviate the above problem, and thus offer a reliable, robust and animal-friendly solution for ongoing measurement of the acidity level of a ruminant animal's stomach fluids.

According to one aspect of the invention the invention, the object is achieved by the initially described bolus, wherein the cavity is configured to receive the ruminal fluids and allow a passage of the ruminal fluids through the bolus. The cavity has walls of a dielectric material, and the sensor means include a coil member encircling the cavity. The coil member is configured to subject the ruminal fluids to an electromagnetic field and under influence thereof measure an electromagnetic property of the ruminal fluids. The acidity measure, in turn, is provided based on the electromagnetic property.

This bolus is advantageous because the fact that the cavity allows a through-passage of the ruminal fluids enables a fully symmetric shape of the bolus, which, in turn, renders the design insensitive to how the bolus is oriented in the reticulum. The bolus design can also be made very durable. Moreover, maintenance is facilitated because after introduction into the animal, no calibration is necessary.

According to one preferred embodiment of this aspect of the invention the invention, the electromagnetic property includes an impedance value. The bolus also includes a processor configured to derive the acidity measure based on the impedance value. Impedance is an appropriate electromagnetic property to study because it is relatively straightforward to measure, for instance via a voltage. Preferably, the bolus further includes a power source connected to the coil member. The power source is here configured to deliver electric energy to the coil member so as to cause the coil member to produce the electromagnetic field.

According to another preferred embodiment of this aspect of the invention, the sensor means includes an interface circuit connecting the coil member to the processor. Thus, registering the electromagnetic property is facilitated.

According to yet another preferred embodiment of this aspect of the invention, the power source and the coil member are configured to produce the electromagnetic field with a relatively narrow spectral range having a distinct center frequency located in an interval from 5 MHz to 15 MHz. Namely, this interval has been found to contain the specific frequencies being most sensitive to acidity variations in water-based fluids.

According to another preferred embodiment of this aspect of the invention, the bolus further includes a pressure sensor module, a mechanical amplifier element and a guide means. The pressure sensor module is configured to transduce pressure signals into electric signals. The pressure signals are here transmitted through the ruminal fluids in the animal's stomach and may be the result of body movements; a heart beat rate, a respiratory rate, a respiratory depth and/or stomach activity of the animal. The mechanical amplifier element extends out from the bolus, is adapted to be surrounded by the fluids, and to absorb mechanical energy from the pressure signals therein. The guide means is configured to convey mechanical energy from the mechanical amplifier element to the pressure sensor module. This design is advantageous because it combines high acoustic sensitivity with mechanical robustness and ample protection for the pressure sensor.

According to a further preferred embodiment of this aspect of the invention, the processor is configured to extract data from the electric signals. The pressure-related data specifically represent at least one of: body movements, a heart beat rate, a respiratory rate, a respiratory depth and stomach activity of the animal. Moreover, the transmitter is configured to receive these data and include the data in the wireless output signal. Hence, additional health-related parameters can be monitored remotely.

According to another aspect of the invention, the object is achieved by the method described initially, wherein the coil member is presumed to encircle a cavity in the bolus, which cavity is configured to receive the ruminal fluids and allow a passage of the ruminal fluids through the bolus, the cavity having walls of a dielectric material, and the method further comprising subjecting the ruminal fluids to the electromagnetic field while passing through the cavity. The advantages of this method, as well as the preferred embodiments thereof, are apparent from the discussion above with reference to the proposed bolus.

According to a further aspect of the invention the object is achieved by a computer program, which is directly loadable into the memory of a computer, and includes software adapted to implement the method proposed above when said program is run on a computer.

According to another aspect of the invention the object is achieved by a computer readable medium, having a program recorded thereon, where the program is to control a computer to perform the method proposed above when the program is loaded into the computer.

Further advantages, beneficial features and applications of the present invention will be apparent from the following description and the dependent claims.

BRIEF DESCRIPTION OF THE DRAWINGS

The invention is now to be explained more closely by means of preferred embodiments, which are disclosed as examples, and with reference to the attached drawings.

DESCRIPTION OF PREFERRED EMBODIMENTS OF THE INVENTION

Typically, the acidity level of a fluid is represented by a pH measure. We will therefore briefly touch upon the definition of pH and the traditional methods for determining this measure.

A pH measurement is a determination of the activity of hydrogen ions in an aqueous solution. Many important properties of a solution can be determined from an accurate measurement of pH, including the acidity of the solution and the extent of a reaction in the solution. Many chemical processes and properties, such as the speed of a reaction and the solubility of a compound, may also depend greatly on the pH level of the solution. In applications ranging from industrial operations to biological processes, it is important to have an accurate and precise measurement of pH.

pH is mathematically defined as the negative logarithm of hydrogen ion activity, i.e. $pH=-\log aH^+$. In most cases, the activity of hydrogen ions in a solution can be approximated by the Molar concentration of hydrogen ions $[H^+]$ in the solution. Hence, $pH \approx -\log [H^+]$.

Using the latter expression, it is straightforward to deduce that a pH of 4 corresponds to a hydrogen ion concentration of $10^{-4}$ Molar.

Further, pH is strongly dependent on the temperature, and the benchmark for pH is actually the concentration of hydrogen ions in water at 25° C. At any temperature, water dissociates into hydrogen ions and hydroxide ions as shown in the following equilibrium reaction:

$$H_2O \leftrightarrow H^+ + OH^-$$

The rate of the equilibrium reaction above is described by an equilibrium constant $K_W$, which varies with temperature, and is equal to $1.01 \times 10^{-14}$ at 25° C. The constant $K_W$ may be determined as: $K_W=[H^+][OH^-]$. Here, it is important to note that the value of $K_W$ varies with temperature, and therefore so does the pH of a solution.

Conventionally, a solution's pH may be measured qualitatively using Litmus paper, or an indicator in solution. Quantitative pH measurements are reliably taken using potentiometric electrodes. These electrodes monitor changes in voltage caused by changes in the activity of hydrogen ions in the solution.

Most modern pH electrodes consist of a single combination of reference and sensing electrode. This type of pH electrode is less complicated and expensive than an electrode-pair design. However, functionally, a combination electrode is the same as an electrode pair. Any pH electrode requires both a sensing electrode and a reference electrode. The sensing electrode has a thin hydrogen permeable membrane containing a solution and an electrode. The membrane of the sensing electrode allows hydrogen ions to slowly pass, creating a positive voltage across the membrane. Of course, the membrane renders the electrode sensitive to mechanical stress, and therefore unsuitable for implementation in a bolus.

The voltage created in the sensing electrode is compared to the voltage in the reference electrode. The voltage difference between the two electrodes is then used to determine the pH of the unknown solution using the Nernst equation:

$$E_{(pH)}=E_{(constant)}+(2.3*RT/nF)*\log[H^+]$$

where:

$E_{(pH)}$=voltage difference between sensing electrode and reference electrode [V]

$E_{(constant)}$=voltage difference in a solution with pH=7 [V]

R=gas constant (8.314 [J/K*mole])

T=temperature [K]

n=number of Valence Electrons per Mole (i.e. 1 for $H^+$)

F=Faraday's Constant (96500 [J/V*mole $e^-$])

By introducing the constants, this equation can be simplified to:

$$E_{(pH)}=E_{(constant)}-1.98158 \times 10^{-4} \text{Volts/Kelvin}*T*pH$$

As can be seen, in the above expression, the only two independent variables are the temperature and the pH. Because both these parameters will affect the voltage output of the electrode, temperature compensation in the calibration is very important for accurate pH measurements.

Although $E_{(constant)}$ is a constant, its value varies between individual electrodes and with temperature. To compensate for this variation, a variable E' is preferably introduced, which is less dependent upon temperature. Most pH electrodes also have sensitivities to pH that deviate slightly from the ideal Nernst equation. To further compensate for such deviations from the Nernst ideal, a variable s may also be introduced. The value of the variable s indicates how well the electrode correlates with the Nernst ideal, with a value of 1 meaning that the electrode does not deviate at all from the ideal. Thus, we obtain the expression:

$$E_{(pH)}=E'*T-1.98158\times10^{-4}*s*T*pH$$

To determine the values of E' and s, the electrode is placed in two different calibration buffers and the respective voltages produced by the electrode are recorded. Two simultaneous equations are then used to determine the values of E' and s. When E' and s are known, the resulting new equation:

$$pH=(E'*T-E_{(pH)})/s*1.98158\times10^{-4}*T$$

may be used to determine the pH based on any voltage and temperature reading. However, for best accuracy, it is recommended that pH readings be taken at a temperature near the temperature where calibration was performed.

The traditional electrode-based pH measurements may indeed provide accurate results. However, clearly, these measurements are complicated and unsuitable for ongoing measurement of the pH-level of an animal's stomach fluids, inter alia due to said calibration requirement.

Figure 1:
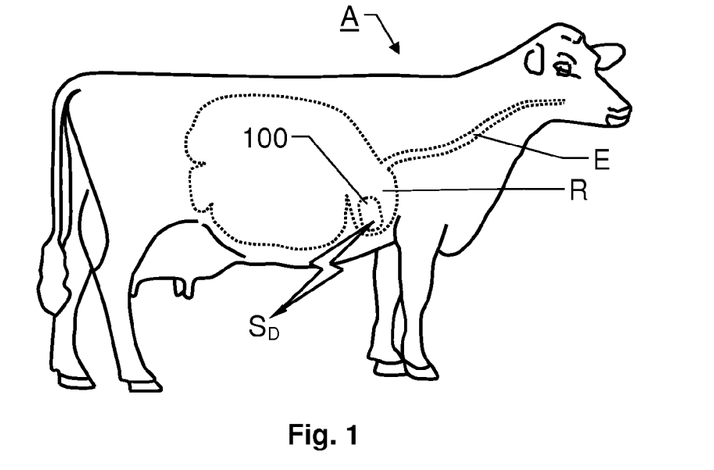
FIG. 1 illustrates a ruminant animal carrying the proposed bolus in its reticulum.

We now refer to FIG. 1, which shows a ruminant animal A carrying the proposed bolus 100 in its reticulum R. Preferably, the bolus 100 is introduced into the reticulum R via the animal's esophagus E. Thus, installing the bolus 100 is an uncomplicated procedure involving no surgery, or the like. The bolus 100 is configured to register at least one health-related parameter, including a measure representative of an acidity level of ruminal fluids in the animal's A stomach, and transmit a wireless output signal $S_D$ reflecting the at least one health-related parameter.

Figure 2A:
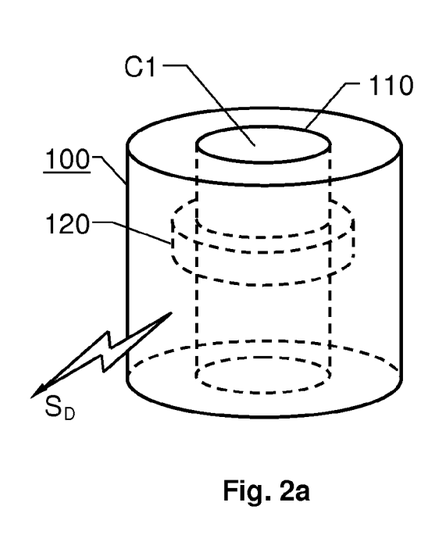
FIGS. 2a-b show perspective views of boluses according to first and second embodiments respectively of the invention.
Figure 2B:
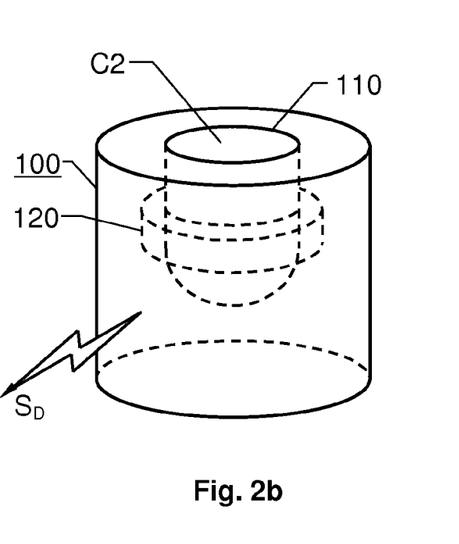

FIG. 2a shows a perspective view of a bolus 100 according to a first embodiment of the invention, and FIG. 2b shows a bolus 100 according to a second embodiment of the invention.

In both embodiments, the bolus 100 includes sensor means 120 configured to register a measure representative of the acidity level of ruminal fluids in an animal's stomach. Furthermore, the bolus 100 includes a transmitter (not shown in FIG. 2a or 2b) configured to transmit the wireless output signal $S_D$.

To expose the sensor means 120 to the ruminal fluids, the bolus 100 has a cavity C1 or C2 respectively. According to the first embodiment shown in FIG. 2a, the cavity C1 is configured to receive the ruminal fluids and allow a passage thereof through the bolus 100, whereas according to the second embodiment shown in FIG. 2b, the cavity C2 has a single opening for both receiving and discharging ruminal fluids. In any case, the cavity C1/C2 has walls 110 of a dielectric material and the sensor means include a coil member 120 encircling the cavity C1/C2. The coil member 120 is configured to subject the ruminal fluids to an electromagnetic field, and under influence thereof measure an electromagnetic property of the ruminal fluids. Based on the electromagnetic property, in turn, the acidity measure is provided, and a wireless output signal $S_D$ reflecting this measure is transmitted from the bolus 100.

Figure 3:
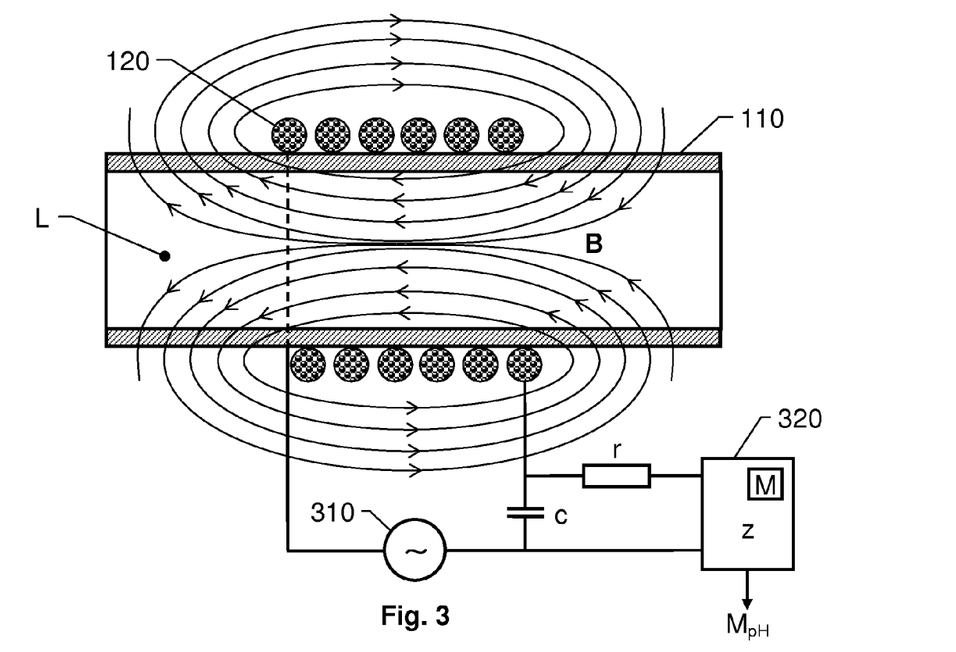
FIG. 3 shows a schematic side view of a measuring circuitry according to one embodiment of the invention.

Referring to FIG. 3, we will describe in further detail how the electromagnetic property z of the ruminal fluids L is registered and how the acidity measure $M_{pH}$ is derived. First, however, we will discuss the relationships between electromagnetic field influence and the properties of liquid media.

The constituents in water based solutions may be detected using the change in water's permittivity ($\epsilon > 80$) at electromagnetic wave frequencies in the range 1 MHz to 200 MHz. This approach is strongly dependent on the concentrations of impurities in the water. Since knowing only the dielectric property is insufficient to draw a conclusion regarding the concentration levels of individual elements, e.g. hydrogen ions [H$^+$], the present invention proposes that dielectric spectroscopy (DS) be applied.

In general, DS (which may also be referred to as impedance spectroscopy) measures the dielectric properties of a medium as a function of frequency. DS is based on the interaction of an external field with the electric dipole moment of a liquid sample. This interaction is often expressed by permittivity.

There are a number of different dielectric mechanisms connected to the way a studied medium reacts to an applied electromagnetic field. Each dielectric mechanism is centered on its characteristic frequency, which is the reciprocal of the characteristic time of the process. Normally, the dielectric mechanisms are divided into relaxation processes and resonance processes, and the most common dielectric mechanisms are: dipole relaxation (in the MHz-to-GHz range), ionic relaxation (in the kHz range) and dielectric relaxation (in the kHz-to-GHz range). The working frequencies for the present invention are in the MHz range (more precisely 5-15 MHz), and therefore dipole relaxation and dielectric relaxation are primarily involved.

Dipole relaxation originates from permanent and induced dipoles aligning to an electric field. The orientation of the dipoles' polarization is disturbed by thermal noise (which misaligns the dipole vectors from the overall direction of the field), and the time needed for the dipoles to relax is determined by the local viscosity of the liquid medium. This renders dipole relaxation heavily dependent on temperature and chemical environment. The polarization of a dielectric material is a competition between torques due to the imposed electric field, which tends to align the molecules; and collisions, which tend to destroy the alignment.

Dielectric relaxation as a whole is the result of the movement of dipoles, i.e. dipole relaxation. Dielectric relaxation is the momentary delay, or lag, in the dielectric constant of a material. This is usually caused by the delay in the molecular polarization with respect to a changing electric field in a dielectric medium.

Ionic relaxation as a whole is the result of electric charges moving due to an applied alternating field. The time lag between electrical field and polarization implies an irreversible degradation of free energy. In physics, dielectric relaxation typically refers to the relaxation response of a dielectric medium to an external electric field of microwave frequencies. Such a relaxation is often described in terms of permittivity as a function of frequency.

The theory of DS gives us an understanding that an electromagnetical field can influence different molecules, and even cells, at a variety of frequencies being unique to each type of molecule or cell. This phenomenon allows quantifying a concentration of hydrogen ions [H$^+$] in liquid substances, such as the ruminal fluids L in an animal's A stomach.

Returning now to FIG. 3, we see a schematic side view of a measuring circuitry included in the bolus 100 according to one embodiment of the invention. The measuring circuitry here contains sensor means in the form of a coil member 120 and a power source 310. The coil member 120 encircles the above-mentioned cavity C1/C2, which in FIG. 3 is represented by a dielectric conduit 110 configured to receive ruminal fluids L. The coil member 120 is configured to subject the ruminal fluids L in the dielectric conduit 110 to an electromagnetic field B. The measuring circuitry is further configured to measure an electromagnetic property, e.g. the impedance value z, of the ruminal fluids L under influence of the electromagnetic field B. Preferably, the measuring circuitry is connected to a processor 320 via an interface circuit. The interface circuit may include a filter, here represented by generic resistive r and capacitive c components, and the processor 320 is configured to derive the acidity measure $M_{pH}$ based on the impedance value z.

It is also preferable if the processor 320 includes, or is associated with, a computer readable medium M, e.g. in the form of a memory module, such that the processor 320 has access to the contents of this medium M. Furthermore, a program is recorded in the computer readable medium M, and the program is adapted to make the processor 320 control the process described above, as well as the embodiments thereof further elaborated on below, when the program is run on the processor.

To generate the electromagnetic field B, the bolus 100 preferably includes a power source 310 connected to the coil member 120. The power source 310 is configured to deliver electric energy to the coil member 120 so as to cause the coil member 120 to produce the electromagnetic field B.

According to a preferred embodiment of the invention, the power source 310 is configured to generate electric power at such a frequency, and the coil member 120 has such characteristics (e.g. number of loops) that the electromagnetic field B is produced with a relatively narrow spectral range having a distinct center frequency located in an interval from 5 MHz to 15 MHz. Namely, the sensitivity to variations in pH typically varies depending on the frequency of electromagnetic field B used. For example, a frequency around 11.2 MHz has been found to be useful for measuring acidity levels in the range pH 4.5 to pH 6.5, while frequencies around 6.7 MHz have been found efficient for measuring acidity levels in the range pH 5.9 to pH 8.3.

Figure 4:
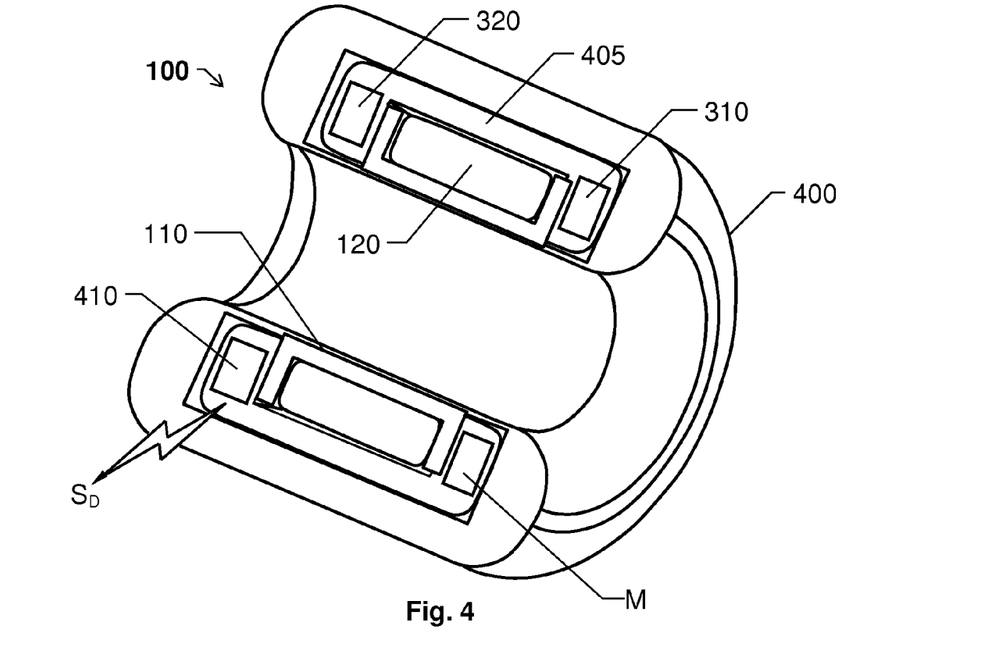
FIG. 4 shows a cross-section view of a bolus according to the first embodiment of the invention.

FIG. 4 shows a cross-section view of a bolus 100 according to the first embodiment of the invention represented in FIG. 2a.

Here, we see the coil member 120 (e.g. an integrated solenoid) of the sensor means encircling the walls 110 of a conduit of dielectric material that form the cavity for receiving ruminal fluids. The power source 310, the processor 320 and the computer readable medium M are likewise visible in FIG. 4.

A transmitter 410 in the bolus 100 is configured to generate and transmit a wireless output signal $S_D$ reflecting a health-related parameter, such as the acidity measure $M_{pH}$, registered by the bolus 100. A battery module 405 is also arranged in the interior of the bolus 100. The battery module 405 is configured to deliver electric power to all the units in the bolus 100, and preferably the battery module 405 has an expected life being at least as long as the expected remaining lifespan of the animal A after having introduced the bolus 100. This means that the battery module 405 should have a considerable capacity, and may thus constitute considerable ballast. The overall weight of the bolus 100 is preferably around 200-300 grams, and the battery module 405 typically represents a substantial portion thereof.

All the components in the bolus 100 are surrounded by a rugged, chemical-protected outer casing 400 (e.g. of so-called germetic plastic) being hermetically sealed, however permeable to the wireless output signal $S_D$.

Figures 5A, 5B, 6:
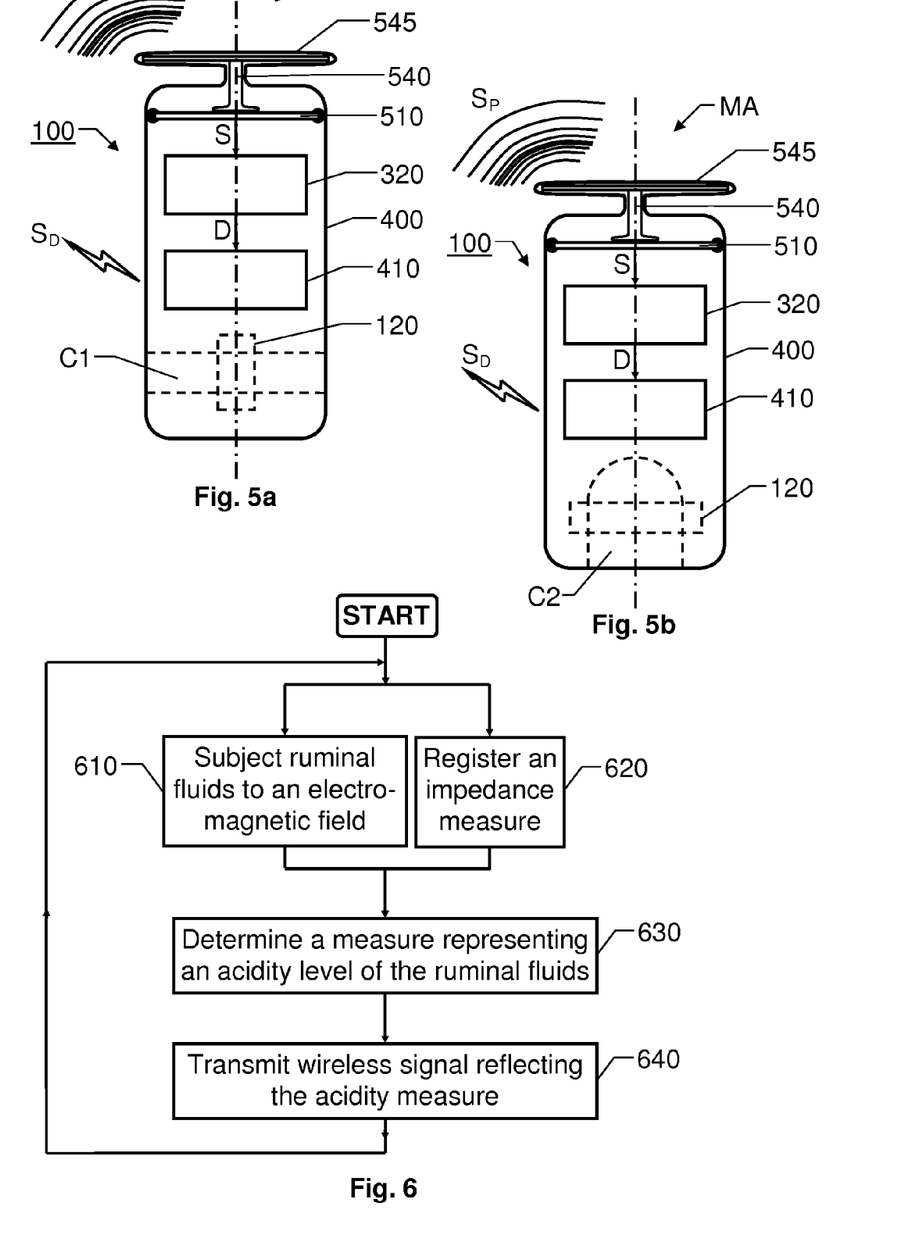
FIGS. 5a-b show cross-section views of boluses according to embodiments of the invention, where the bolus is further configured to register pressure signals.
FIG. 6 illustrates, by means of a flow diagram, the general method according to the invention.

In FIGS. 5a and 5b, we see cross-section views of boluses 100 according to embodiments of the invention, where each bolus 100 is further configured to register pressure signals $S_p$. For reasons of clarity, the sensor means 120 for registering the signals based upon which the at least one health-related parameter is determined is outlined schematically. FIG. 5a shows a bolus 100 according to a first embodiment containing a cavity C1 that is configured to receive the ruminal fluids L and allow a passage thereof through the bolus 100. FIG. 5b shows a bolus 100 according to a second embodiment containing a cavity C2 with a single opening for both receiving and discharging ruminal fluids L. Otherwise, the boluses 100 in FIGS. 5a and 5b have essentially the same design.

In both cases, the bolus 100 is configured to register pressure signals. $S_p$ transmitted through fluids L in the reticulum R. To this aim, the bolus 100 has a casing 400, which is adapted to be immersed in said fluids while preventing the fluids L from reaching an interior of the casing 400. The casing 400 is preferably made of a polymeric material being transparent to radio waves, such as natural rubber, nylon, PVC or polystyrene. The interior of the casing 400 contains a pressure sensor module 510 configured to produce electric signals S.

A mechanical amplifier element MA extends out from the casing 400. The mechanical amplifier element MA is adapted to be surrounded by the fluids in the reticulum and absorb mechanical energy from the pressure signals $S_p$. Preferably, the mechanical amplifier element MA has a receiver surface 545, which is configured to be repositioned in response to the pressure signals $S_p$ (essentially move up and down given the orientation in FIGS. 5a and 5b) and thus function as an energy receiver. For practical reasons it is further advantageous if the receiver surface 545 of the amplifier element MA has an overall circular shape. Namely, thereby for a given maximum area of the surface, the risks are minimized that the amplifier element MA injures the animal or interferes significantly with the digestive function when the bolus 100 is being tossed around in the reticulum R. The receiver surface 145 is operatively connected to a guide means 540 that is configured to convey mechanical energy from the mechanical amplifier element MA to the pressure sensor module 510. Thus, the receiver surface 545 and the guide means 540 are preferably relatively rigid, while a top part of the bolus 100 towards the receiver surface 545 and the guide means 540 is flexible, so that any movements of the receiver surface 545 will cause the guide means 540 to influence the pressure sensor module 510.

In FIGS. 5a and 5b, the receiver surface 545 contains substantially flat surface. However, alternatively, the mechanical amplifier element MA may include a dome-shaped receiver surface configured to receive and convey energy from the pressure signals $S_p$ to the pressure sensor module 510.

The pressure sensor module 510 is configured to transduce any pressure signals forwarded via the guide means 540 into electric signals S. These signals, in turn, form a basis for data D produced by the processor 320. The data D may here represent: body movements, a heart beat rate, a respiratory rate, a respiratory depth and/or stomach activity of the animal A.

The transmitter 410 is configured to receive the data D and include the data D in the wireless output signals $S_D$ transmitted from the animal A. Thus, to attain an efficient output of the data D for further processing and/or presentation to a user, it is advantageous if the transmitter 410 has access to a radio interface, which is configured to generate radio signals representing the output signals $S_D$. However, technically, alternative technologies are also conceivable, such as transmitting the output signals $S_D$ via magnetic resonance. It is further preferable if the bolus 100 is equipped with an on/off switch that is controllable from outside the animal A, e.g. a radio interface, so that the bolus 100 can be selectively activated/deactivated in a straightforward manner.

Anyhow, the bolus 100 preferably has a general cylinder shape because this facilitates the introduction of the bolus 100 into the animal A via the esophagus E. Said general cylinder has first and second short sides, and the mechanical amplifier element MA is arranged to extend from the first short side (top side in FIGS. 5a and 5b). The length of the bolus 100 is preferably 75-145 mm and the width is preferably 20-60 mm.

It has been found that the sensor in the pressure sensor module 510 has the best sensitivity if the first short side (where the mechanical amplifier element MA is located) points in a general upward direction when the bolus 100 is installed in the animal A. To increase the probability that the bolus 100 is oriented this way, it is advantageous if the bolus 100 includes ballast having such weight and position relative to the total contents of the bolus 100 that a center of gravity of the bolus 100 is located closer to the second short side than the first short side. This renders the bolus 100 balanced by the ballast and the buoyancy, such that the first short side with the mechanical amplifier element points in a general upward direction when the bolus 100 is installed in the animal, Thereby, the sensor attains good sensitivity.

In order to sum up, we will now describe the general method according to the invention with reference to the flow diagram in FIG. 6.

In a first step 610, the ruminal fluids of a reticulum in which the proposed bolus is located are subjected to an electromagnetic field. A step 620, parallel to step 610, registers an impedance measure of the ruminal fluids. Then, based on the impedance measure, a step 630 determines a measure representing an acidity level of the ruminal fluids. Subsequently, a step 640 transmits a wireless signal reflecting the acidity measure determined in step 630. Thereafter, the procedure loops back to steps 610 and 620.

All of the process steps, as well as any sub-sequence of steps, described with reference to FIG. 6 above may be controlled by means of a programmed computer apparatus. Moreover, although the embodiments of the invention described above with reference to the drawings comprise computer apparatus and processes performed in computer apparatus, the invention thus also extends to computer programs, particularly computer programs on or in a carrier, adapted for putting the invention into practice. The program may be in the form of source code, object code, a code intermediate source and object code such as in partially compiled form, or in any other form suitable for use in the implementation of the process according to the invention. The program may either be a part of an operating system, or be a separate application. The carrier may be any entity or device capable of carrying the program. For example, the carrier may comprise a storage medium, such as a Flash memory, a ROM (Read Only Memory), for example a DVD (Digital Video/Versatile Disk), a CD (Compact Disc) or a semiconductor ROM, an EPROM (Erasable Programmable Read-Only Memory), an EEPROM (Electrically Erasable Programmable Read-Only Memory), or a magnetic recording medium, for example a floppy disc or hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant processes.

Although the invention is advantageous in connection with cow milking, the invention is equally well adapted for implementation in milking machines for any other kind of mammals, such as goats, sheep or buffaloes.

The term "comprises/comprising" when used in this specification is taken to specify the presence of stated features, integers, steps or components. However, the term does not preclude the presence or addition of one or more additional features, integers, steps or components or groups thereof.

The invention is not restricted to the described embodiments in the figures, but may be varied freely within the scope of the claims.

The invention claimed is:

1. A bolus for introducing into a ruminant animal's (A) reticulum (R) and for ongoing measurement of an acidity level of an animal's stomach fluids, the bolus (100) comprising:
a housing (100) having an outermost surface exterior wall;
a cavity defined by a portion of the exterior wall of the housing, the cavity (C1, C2) having a wall of dielectric material and at least a first opening for receiving ruminal fluids into the cavity, the wall defining a dielectric conduit (110), the first opening being an unobstructed opening freely allowing the ruminal fluids from the animal's (A) reticulum (R) to be received into the cavity;
a power generator (310) that generates electric power within a spectral range;
a sensor coil (120) encircling the dielectric conduit (110) and powered by the power generator, the sensor coil (120) configured to subject the received ruminal fluids (L) within the cavity to an electromagnetic field (B) within the spectral range;
a processor (320) connected to the sensor coil (120) to measure, under influence of the electromagnetic field (B), an electromagnetic property (z) of the ruminal fluids (L),
wherein from the measure of the electromagnetic property (z), the processor (320) determines an acidity measure ($M_{pH}$) of an acidity level of the ruminal fluids (L); and
a transmitter (410) connected to the processor (32) and configured to transmit a wireless output signal ($S_D$) reflecting the determined acidity measure ($M_{pH}$),
wherein the power generator (310), the sensor coil (120), the processor (320), and the transmitter (410) are each located within the housing (100).

2. The bolus of claim 1, wherein,
the spectral range includes a distinct center frequency within 5 Mhz through 15 MHz,
the electromagnetic property (z) is impedance of the ruminal fluids (L), and
the processor (320) is configured to derive the acidity measure ($M_{pH}$) from the measured impedance of the ruminal fluids (L).

3. The bolus of claim 1, wherein the dielectric conduit (110) is closed at one end and the first opening is further configured for discharging the received ruminal fluids.

4. The bolus of claim 1, wherein,
the dielectric conduit (110) further comprises a second opening opposite the first opening, the second opening allowing the ruminal fluids to be discharged from the dielectric conduit (110) of the cavity, and the cavity defines a passage through the housing (100) allowing the received ruminal fluids passage through the dielectric conduit (110) from the first opening to the second opening.

5. The bolus of claim 4, wherein,
the passage extends in a longitudinal direction running from a first end of the housing to a second end of the housing.

6. The bolus of claim 4, wherein,
the passage extends in a direction transverse to the longitudinal direction.

7. The bolus of claim 1, wherein,
an overall weight of the bolus is in a range of from 200 to 300 grams, and
the housing is sized for placement in the reticulum of a cow.

8. The bolus of claim 1, further comprising a battery (405), wherein,
the power generator (310) is powered by the battery (405),
the battery (405) is located within the housing (100), and
the battery is sized based on a lifespan of a cow.

9. The bolus of claim 1, wherein,
the cavity is located proximate a first end of the housing, and, at an opposite, second end of the housing, the bolus further comprises:
a pressure sensor module (510) configured to transduce pressure signals ($S_p$) into electric signals (S), said pressure signals ($S_p$) being transmitted through the ruminal fluids (L) in the animal's (A) stomach;
a mechanical amplifier element (MA) extending out from the first end of the housing, the mechanical amplifier element (MA) being adapted to be surrounded by the fluids (L) and absorb mechanical energy from the pressure signals ($S_p$), and
a guide element (540) configured to convey mechanical energy from the mechanical amplifier element (MA) to the pressure sensor module (110).

10. The bolus of claim 1, wherein the cavity further comprises a second opening opposite the first opening, the second opening for discharging the received ruminal fluids, the second opening being an unobstructed opening freely allowing the ruminal fluids to be discharged from the dielectric conduit (110) of the cavity.

11. The bolus of claim 1, wherein,
the processor (320) is further configured to extract data (D) from the electric signals (S), the data (D) representing at least one of: body movements, a heart beat rate, a respiratory rate, a respiratory depth and stomach activity of the animal (200); and
the transmitter (410) is further configured to receive the data (D) and include the data (D) in the wireless output signal ($S_D$).

12. The bolus of claim 8, wherein,
an overall length of the bolus is in a range from 75 to 145 mm, and
an overall width of the bolus is in a range from 20 to 60 mm.

13. A method for repeatedly determining at least one health-related parameter for the animal (A), the method comprising:
using a bolus (100) located in the animal's (A) reticulum (R), the bolus (100) comprising
an overall housing (100) having an outermost surface exterior wall,
a cavity defined by a portion of the exterior wall of the housing, the cavity (C1, C2) having a wall of dielectric material and at least a first opening for receiving ruminal fluids into the cavity, the wall defining a dielectric conduit (110), the first opening being an unobstructed opening freely allowing the ruminal fluids from the animal's (A) reticulum (R) to be received into the cavity,
a power generator (310) that generates electric power within a spectral range,
a sensor coil (120) encircling the dielectric conduit (110) and powered by the power generator, the sensor coil (120) configured to subject the received ruminal fluids (L) within the cavity to an electromagnetic field (B) within the spectral range,
a processor (320) connected to the sensor coil (120) to measure, under influence of the electromagnetic field (B), an electromagnetic property (z) of the ruminal fluids (L),
wherein from the measure of the electromagnetic property (z), the processor (320) determines an acidity measure (MpH) of an acidity level of the ruminal fluids (L), and
a transmitter (410) connected to the processor (32) and configured to transmit a wireless output signal (SD) reflecting the determined acidity measure (MpH),
wherein the power generator (310), the sensor coil (120), the processor (320), and the transmitter (410) are each located within the housing (100);
with sensor coil (120) subjecting the received ruminal fluids (L) within the cavity to an electromagnetic field (B) within the spectral range, registering, via the sensor coil (120) and the processor (320), the acidity measure (MpH) of the ruminal fluids (L); and
transmitting, via the transmitter (410), the wireless output signal ($S_D$) reflecting the determined acidity measure (MpH).

14. The method of claim 13, wherein,
the spectral range includes a distinct center frequency within 5 Mhz through 15 MHz.

15. The method of claim 13, wherein,
the electromagnetic property (z) is impedance of the ruminal fluids (L), and
the processor (320) is configured to derive the acidity measure ($M_{pH}$) from the measured impedance of the ruminal fluids (L).

16. The method of claim 13, wherein,
the cavity of the bolus further comprises a second opening opposite the first opening, the second opening for discharging the received ruminal fluids, the second opening allowing the ruminal fluids to be discharged from the dielectric conduit (110) of the cavity, the cavity defines a passage through the housing (100) allowing the received ruminal fluids passage through the dielectric conduit (110), and
said registering step occurs with the ruminal fluids passing within the dielectric conduit.

17. The method of claim 16, wherein the passage extends in a longitudinal direction running from a first end of the housing to a second end of the housing.

18. The method of claim 16, wherein the passage extends transverse to a longitudinal direction running from a first end of the housing to a second end of the housing.

19. The method of claim 13, wherein,
the bolus further comprises a battery (405),
the power generator (310) is powered by the battery (405),
the battery (405) is located within the housing (100), and
the battery is sized based on a lifespan of a cow.

20. The method of claim 19, wherein,
the cavity is located proximate a first end of the housing, and, at an opposite, second end of the housing, the bolus further comprises
a pressure sensor module (510) configured to transduce pressure signals ($S_p$) into electric signals (S), said pressure signals ($S_p$) being transmitted through the ruminal fluids (L) in the animal's (A) stomach;

a mechanical amplifier element (MA) extending out from the first end of the housing, the mechanical amplifier element (MA) being adapted to be surrounded by the fluids (L) and absorb mechanical energy from the pressure signals ($S_p$), and a guide element (540) configured to convey mechanical energy from the mechanical amplifier element (MA) to the pressure sensor module (110), the method further comprising:

from the pressure sensor module, operating the processor (320) to extract data (D) from the electric signals (S), the data (D) representing at least one of body movements, a heart beat rate, a respiratory rate, a respiratory depth, and stomach activity of the animal (200); and using the transmitter (410), transmitting the extracted data (D) in the wireless output signal ($S_D$).

21. A non-transitory computer readable medium (M) having a program recorded thereon, execution of the program causing computer control to repeatedly determine at least one health-related parameter for the animal (A), the method comprising:

using a bolus (100) located in the animal's (A) reticulum (R), the bolus (100) comprising a housing (100) having an outermost surface exterior wall, a cavity defined by a portion of the exterior wall of the housing, the cavity (C1, C2) having a wall of dielectric material and at least a first opening for receiving ruminal fluids into the cavity, the wall defining a dielectric conduit (110), the first opening being an unobstructed opening freely allowing the ruminal fluids from the animal's (A) reticulum (R) to be received into the cavity, a power generator (310) that generates electric power within a spectral range, a sensor coil (120) encircling the dielectric conduit (110) and powered by the power generator, the sensor coil (120) configured to subject the received ruminal fluids (L) within the cavity to an electromagnetic field (B) within the spectral range, a processor (320) connected to the sensor coil (120) and under the computer control, to measure, under influence of the electromagnetic field (B), an electromagnetic property (z) of the ruminal fluids (L), wherein, under the computer control, from the measure of the electromagnetic property (z), the processor (320) determines an acidity measure (MpH) of an acidity level of the ruminal fluids (L), and a transmitter (410) connected to the processor (32) and configured to transmit a wireless output signal (SD) reflecting the determined acidity measure (MpH), wherein the power generator (310), the sensor coil (120), the processor (320), and the transmitter (410) are each located within the housing (100);

with sensor coil (120) subjecting the received ruminal fluids (L) within the cavity to an electromagnetic field (B) within the spectral range, registering, via the sensor coil (120) and the processor (320), the acidity measure (MpH) of the ruminal fluids (L); and transmitting, via the transmitter (410), the wireless output signal ($S_D$) reflecting the determined acidity measure (MpH).

* * * * *